US012582321B2

(12) United States Patent
Chu et al.

(10) Patent No.: US 12,582,321 B2
(45) Date of Patent: Mar. 24, 2026

(54) CARDIAC DIASTOLIC FUNCTION ASSESSMENT METHOD, DEVICE, AND SYSTEM

(71) Applicant: SHENZHEN DARMA TECHNOLOGY CO., LTD., Shenzhen (CN)

(72) Inventors: Zhengpei Chu, Shenzhen (CN); Dongdong Zhao, Shenzhen (CN); Lingjun Zeng, Shenzhen (CN); Pengbo Liu, Shenzhen (CN); Shaochun Zhuang, Shenzhen (CN)

(73) Assignee: CARDIOSTORY INC., Lewes, DE (US)

( * ) Notice: Subject to any disclaimer, the term of this patent is extended or adjusted under 35 U.S.C. 154(b) by 1158 days.

(21) Appl. No.: 17/613,033

(22) PCT Filed: May 20, 2019

(86) PCT No.: PCT/CN2019/087632
§ 371 (c)(1),
(2) Date: Nov. 19, 2021

(87) PCT Pub. No.: WO2020/232604
PCT Pub. Date: Nov. 26, 2020

(65) Prior Publication Data
US 2022/0248962 A1     Aug. 11, 2022

(51) Int. Cl.
*A61B 5/021*          (2006.01)
*A61B 5/00*           (2006.01)

(52) U.S. Cl.
CPC ............ *A61B 5/021* (2013.01); *A61B 5/7285* (2013.01); *A61B 2562/0219* (2013.01); *A61B 2562/0261* (2013.01)

(58) Field of Classification Search
CPC .................. A61B 5/021; A61B 5/7285; A61B 2562/0219; A61B 2562/0261; A61B 5/02028; A61B 5/7278; A61B 5/0205; A61B 5/332; A61B 5/7267; A61B 5/339; A61B 5/7282; A61B 7/003; A61B 5/055; A61B 5/725; A61B 8/4416; A61B 5/08;
(Continued)

(56) References Cited

U.S. PATENT DOCUMENTS 5,178,151 A      1/1993  Sackner
5,853,005 A *   12/1998  Scanlon ............... A61B 5/6896
                                                        381/166
(Continued)

FOREIGN PATENT DOCUMENTS

CN          107427260 A      12/2017

*Primary Examiner* — Alex M Valvis
*Assistant Examiner* — Chanel J Jhin
(74) *Attorney, Agent, or Firm* — Cheng-Ju Chiang

(57) ABSTRACT

A cardiac diastolic function assessment method, for use in the field of cardiac monitoring. The method comprises: noninvasively acquiring vibration information of the thoracic body surface of a subject; preprocessing the vibration information to generate hemodynamics-related information; determining a first parameter and a second parameter on the basis of the hemodynamics-related information; generating an indicating parameter on the basis of the first parameter and of the second parameter, and assessing the cardiac diastolic function of the subject on the basis of the indicating parameter.

9 Claims, 9 Drawing Sheets

100

(58) Field of Classification Search
CPC ... A61B 5/0044; A61B 5/0245; A61B 5/1102;
 A61B 5/6833; G06F 18/2135; G06N 3/08
USPC ........................................................ 600/595
See application file for complete search history.

(56) References Cited

U.S. PATENT DOCUMENTS

| | | | |
|---|---|---|---|
| 10,743,797 B2 * | 8/2020 | Hu .................... | A61B 5/1126 |
| 2007/0055170 A1 | 3/2007 | Lippert et al. | |
| 2014/0275976 A1 | 9/2014 | Moro | |
| 2015/0038856 A1 | 2/2015 | Houlton et al. | |

* cited by examiner

100

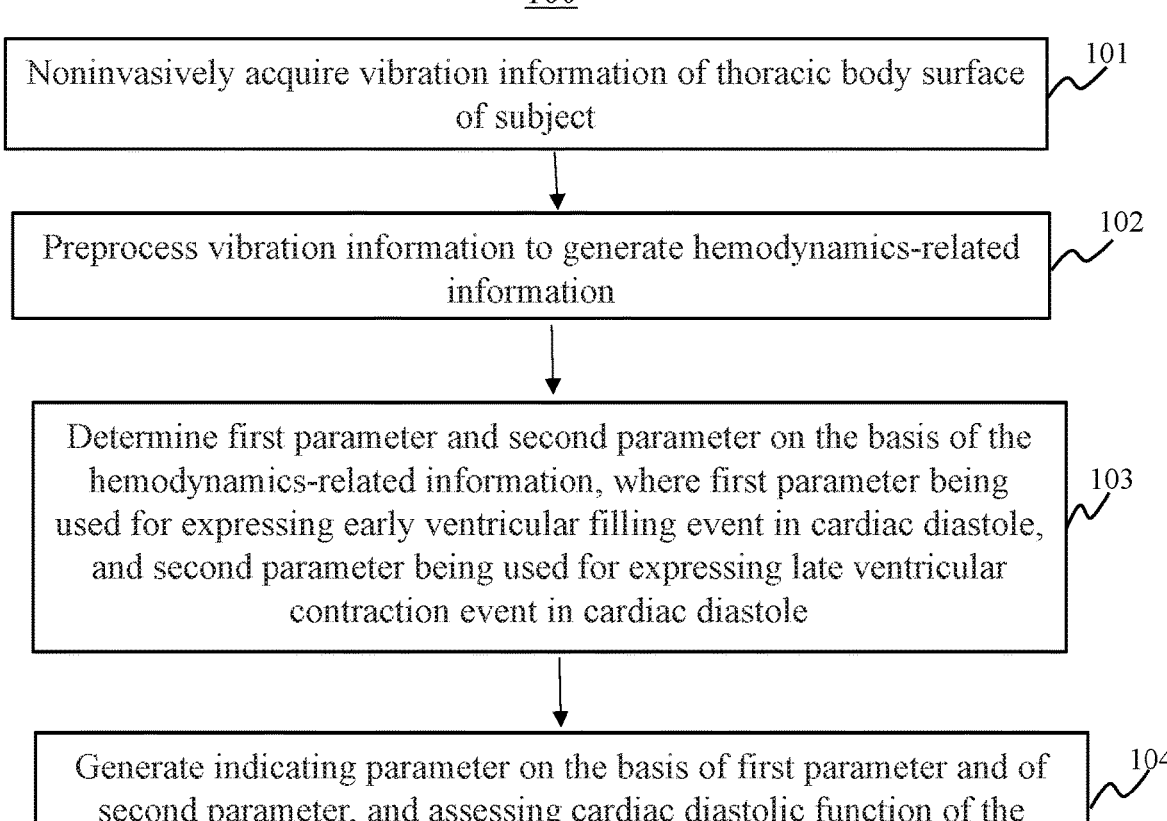

| Noninvasively acquire vibration information of thoracic body surface of subject | 101 |

Preprocess vibration information to generate hemodynamics-related information — 102

Determine first parameter and second parameter on the basis of the hemodynamics-related information, where first parameter being used for expressing early ventricular filling event in cardiac diastole, and second parameter being used for expressing late ventricular contraction event in cardiac diastole — 103

Generate indicating parameter on the basis of first parameter and of second parameter, and assessing cardiac diastolic function of the subject on the basis of indicating parameter — 104

FIG. 1

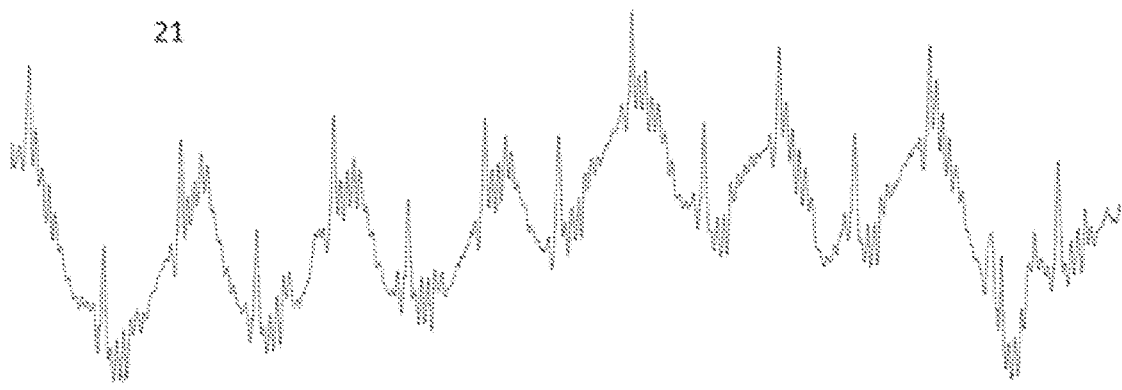

**ROC Curve of ventricular filling pressure assessment based on indicating parameter *I1***

**ROC Curve of ventricular filling pressure assessment based on indicating parameter *I2***

**ROC Curve of ventricular filling pressure assessment based on indicating parameter *I3***

300

CARDIAC DIASTOLIC FUNCTION ASSESSMENT METHOD, DEVICE, AND SYSTEM

CROSS REFERENCE TO RELATED APPLICATIONS

The present application is a 35 U.S.C. § 371 National Phase conversion of International (PCT) Patent Application No. PCT/CN2019/087632, filed on May 20, 2019, the disclosure of which is incorporated by reference herein. The PCT International Patent Application was filed and published in Chinese.

FIELD OF THE INVENTION

The present invention relates to the field of cardiac monitoring, and particularly relates to a non-invasive diastolic function assessment method, device, and system.

BACKGROUND OF THE INVENTION

Heart failure (abbreviated as HF) is a clinical syndrome with multiple etiologies and pathogenesis. With the aging of the population and an increasing survival rate of patients with acute myocardial infarction, the number of patients with chronic heart failure is increasing rapidly. Patients with heart failure suffer from a chronic state to an acute worsening state, and suffer from an accompanied elevated filling pressure. Elevated filling pressure will cause the heart's function to enter a rapid vicious circle, but the patient itself will not feel the symptoms until the filling pressure continues to rise for about 20 days and need to be admitted to the hospital urgently; while at this time, the impairment of the heart function is caused and is irreversible. When the patient is identified in an elevated filling pressure status, timely intervention is required to avoid further deterioration. This has become the consensus of clinicians.

At present, there are implantable products used to evaluate the diastolic function, but the cost is relatively high, and if it is only used for monitoring, patients are less likely to accept. Therefore, a more friendly and more convenient product is needed for monitoring the diastolic function.

SUMMARY OF THE INVENTION

Technical Problem

An object of the present invention is to provide a method, device, system, and computer-readable storage medium for accessing a cardiac diastolic function of a subject; and aims to realize a non-invasive evaluation of the diastolic function of the heart.

Solutions to the Problem

Technical Solutions

In a first aspect, the present invention provides a cardiac diastolic function assessment method, comprising steps of:
  acquiring vibration information on a body surface corresponding to a subject's thoracic cavity in a noninvasive manner;
  preprocessing the vibration information to generate hemodynamic-related information;
  determining a first parameter and a second parameter on the basis of the hemodynamics-related information;

where the first parameter represents a ventricular filling event during early ventricular diastole, and the second parameter represents an atrial systole event during late ventricular diastole; and
  generating an indicating parameter on the basis of the first parameter and of the second parameter; and assessing the cardiac diastolic function of the subject on the basis of the indicating parameter.

In a second aspect, the present invention provides a computer-readable storage medium having computer programs stored thereon, which when being executed by a processor, cause the processor to perform the steps of the above-mentioned cardiac diastolic function assessment method.

In a third aspect, the present invention provides a diastolic function assessment device, comprising: one or more processors; a memory; and one or more computer programs, wherein the one or more computer programs are stored in the memory, and configured to be executed by the one or more processors; and the one or more processors execute the one or more computer programs to perform the steps of the above-mentioned diastolic function assessment method.

In a fourth aspect, the present invention provides a cardiac diastolic function assessment system, comprising:
  one or more vibration sensors for acquiring vibration information on a body surface corresponding to a subject's thoracic cavity surface; and
  the diastolic function assessment device, as described above, connected to the one or more vibration sensors.

Advantages of the Preset Invention

Advantages

The method of the present invention monitors the diastolic function by acquiring the vibration information of the subject without intruding his body, it is a passively measuring, and can realize continuous monitoring. The subject only needs to lie on the measuring device to perform the measurement, and no need for professional assistance. The method has the advantages of high measurement accuracy and simple operation, can improve the comfort of the tester, and can be applied to scenes such as hospitals and homes. The diastolic function assessment system provided in the present invention can evaluate the diastolic function of the subject, and then prompt a warning in advance when deterioration appear, so as to help the subject avoid deterioration.

BRIEF DESCRIPTION OF THE DRAWINGS

FIG. 1 is a flowchart of a cardiac diastolic function assessment method in accordance with a first embodiment of the present invention;

FIG. 2 is a waveform diagram of vibration information of the subject A acquired by a fiber-optic sensor;

DETAILED DESCRIPTION OF THE INVENTION

Figure 3:
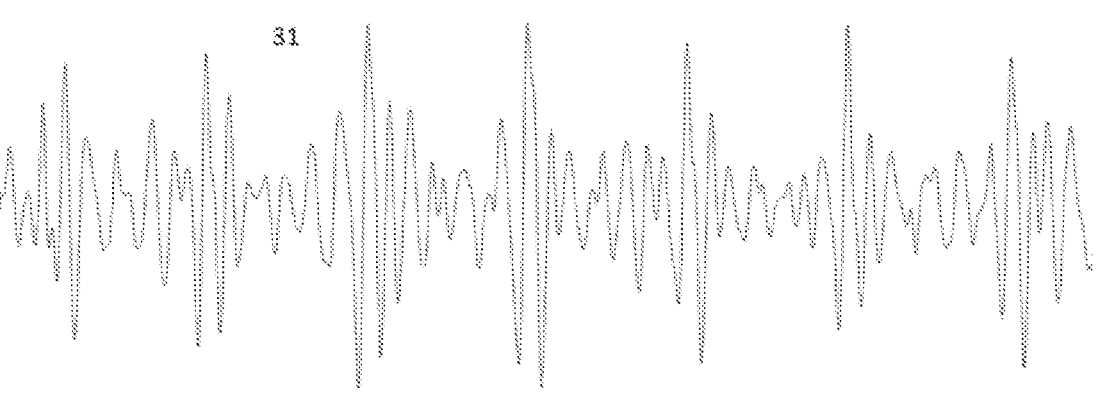
FIG. 3 is a diagram of time-domain waveforms of hemodynamic related information.

In order to make the objects, technical solutions, and advantages of the present invention clearer, the present invention will be further described in detail below in conjunction with the accompanying drawings and embodiments. It should be understood that the specific embodiments described here are only used to explain the present invention, but not to limit the present invention.

As used in the description and claims, the terms "a", "an" and "the" comprise both singular and plural references unless the context clearly dictates otherwise. Generally, the term "includes" or "comprise" is intended to mean the steps or elements that have been clearly identified, and these steps or elements do not constitute an exclusive list, and the method or device can also comprise other steps or elements.

In order to illustrate the technical solutions of the present invention, the following is explained through specific embodiments.

First Embodiment

Referring to FIG. 1, a diastolic function assessment method 100 provided in the first embodiment of the present invention comprises the following steps. It should be noted that if there are substantially the same results, the diastolic function assessment method of the present invention is not limited to the flowchart sequence shown in FIG. 1.

S101: acquiring vibration information on a body surface corresponding to a subject's thoracic cavity in a noninvasive manner.

In the first embodiment of the present invention, one or more vibration sensors may be used for acquiring vibration information on a body surface corresponding to a subject's thoracic cavity in a noninvasive manner. The vibration sensor can be an acceleration sensor, a speed sensor, a displacement sensor, a pressure sensor, a strain sensor, or a stress sensor. In addition, the vibration sensor can also be a sensor that converts physical quantities equivalently on the basis of acceleration, speed, displacement, or pressure (such as electrostatic sensor, inflatable pressure sensor, radar sensor, etc.). The strain sensor can be a fiber-optic sensor. In the first embodiment of the present invention, other means such as a photoelectric sensor can also be used for acquiring vibration information on a body surface corresponding to a subject's thoracic cavity in a noninvasive manner.

In the first embodiment, acquiring vibration information on a body surface corresponding to a subject's thoracic cavity using a fiber-optic sensor. The fiber-optic sensor can be placed under the subject's body. For example, the subject can be in a posture such as supine, prone, side-lying, etc. The fiber-optic sensor can be placed on the bed, and the subject is supine (prone or side-lying) on it. Taking the subject in a supine position as an example, the preferable measurement position is that the fiber-optic sensor is placed under the subject's back, and preferably, the fiber-optic sensor is placed under the body surface area between the subject's left and right shoulder blades, that is, under the middle shoulder. For ease of description, the body surface between the left and right shoulder blades of the subject is defined as the middle shoulder. Those of ordinary skill in the art can understand that when the subject lies in the prone position, corresponding to the measurement position when the subject is in the supine posture, for example, the subject's chest is the measurement position corresponding to the back of the subject in the supine position. The vibration sensor can also be placed on the contact surface behind the back of the subject in the supine posture at a certain tilt angle or on the contact surface behind the back of the subject leaning on a wheelchair or other leaning objects to acquire the vibration information. In addition, the vibration sensor can also be placed above the body of the subject in a supine position. For example, an acceleration sensor can be placed on the chest surface area corresponding to the apex of the subject's heart.

At least one vibration sensor is used in the present invention. When multiple vibration sensors are used, each sensor works independently and synchronously. The size of each sensor can be the same or different, such as 20 cm*30 cm or 5 cm*4 cm. Sensors with any size can be arranged and combined in any way. For example, in some embodiments, a thinner subject can be provided with one large sensor or two small sensors, while a subject with a wider body can be provided with two large sensors or a combination of two small sensors and one large sensor. When a fiber-optic sensor is used as the vibration sensor, at least one fiber-optic sensor is placed under the right shoulder of the subject. The fiber-optic sensor can be placed directly under the subject's body or placed under a mattress in indirect contact with the subject. In some examples, a sense area of the fiber-optic sensor is at least 20 square centimeters, where the sense area refers to the area of the vibration sensor used to sense vibration (for example, the sense area of a fiber-optic sensor refers to the area where the optical fibers are distributed in the fiber-optic sensor).

FIG. 2 shows vibration information waveform of the subject acquired by a fiber-optic sensor, where the horizontal axis of the curve 21 represents time, and the vertical axis represents normalized vibration information, which is dimensionless. The vibration information acquired by the vibration sensor includes respiratory signal component and the hemodynamic signal component, but also the interferences caused by environmental micro-vibration and body movement, as well as the noise signal of the circuit itself. The large outline of the signal at this time is the respiration envelope, and the hemodynamic signal and other interference are superimposed on the respiration envelope curve.

S102: preprocessing the vibration information to generate hemodynamic-related information.

The vibration information obtained by different sensors contains different amounts of information, some contain relatively rich information, thus need to be preprocessed to obtain desired signals. For example, when a fiber-optic sensor is used as the vibration sensor, the acquired vibration information includes the subject's breathing signal, body motion signal, hemodynamic signal, and inherent noise of the sensor.

In the first embodiment of the present invention, S102 may specifically comprise:

performing at least one of: filtering, noise removal and signal scaling on the vibration information to obtain hemodynamic related information. Specifically, according to the desired characteristics of the filtered signal, filtering the vibration information to remove noise using one or more of: IIR filter, FIR filter, wavelet filter, zero-phase bidirectional filter, polynomial smoothing filter, integral transform, and differential transformation. For example, filtering the vibration information below 1 Hz to remove breathing signals and body motion signals. Preprocessing may also comprise steps of: determining whether the vibration information carrying power-line interference, and if yes, using a power frequency filter to remove power-line interference; or, further, removing high-frequency interference (for example, above 45 Hz). The processed information can be scaled according to specific conditions to obtain hemodynamic related information. Or, filtering the vibration signal by directly setting a filter interval such as any interval between 1 Hz-50 Hz.

FIG. 3 illustrates a time-domain waveform diagram of hemodynamic related information after preprocessing the vibration information of FIG. 2 acquired by the fiber-optic sensor, and a filtering interval of the curve 31 is 9 Hz-45 Hz. Each waveform of the curve 31 has obvious characteristics and good consistency, regular periodicity, clear outline, and stable baseline, that is, the signal quality is better.

S103: determining a first parameter and a second parameter on the basis of the hemodynamics-related information; where the first parameter represents a ventricular filling event during early ventricular diastole, and the second parameter represents an atrial systole event during late ventricular diastole.

In the first embodiment, S103 may specifically comprise the following steps of S1031 to S1033

S1031: processing the hemodynamic related information to generate first high-frequency component information, second high-frequency component, and vibration energy information; where the first high-frequency component information represents the speed signal; the second high-frequency component information represents the acceleration signal; and the vibration energy information represents the energy signal.

A cycle beating of the heart will cause periodic phenomena of various changes, such as periodic changes in intracardiac pressure and cardiovascular pressure, the volume of both atria and the ventricles, opening and closing of the heart valves (including mitral valve, tricuspid valve, aortic valve, pulmonary artery), and blood flow velocity, etc. These periodic changes drive blood flowing in a certain direction in the blood vessels. Hemodynamics is the study of the mechanics of blood flow in the cardiovascular system, and takes blood flow and the of blood vessel deformation as the research object. The "hemodynamic related information" described in the present invention refers to any information related to hemodynamics, and may comprise, but is not limited to, one or more of: information related to producing blood flow (for example, atrial systole and relaxation causes ejection), information related to the dynamics of blood flow (such as CO (cardiac output), left ventricular ejection impacting the aortic arch), information related to blood flow pressure (such as systolic blood pressure, diastolic blood pressure, mean arterial pressure), and blood vessel-related information (such as blood vessel elasticity, etc.). The periodic beating of the heart can maintain blood circulation. Therefore, various parameters related to heartbeat, such as the opening and closing of the heart valve, changes in the volume of both the atria and ventricles, changes in the pressures of the atria and the ventricles, and the flow rate and direction of blood flow in the atria and ventricles. et., which are all hemodynamic related information.

The vibration information obtained through the fiber-optic sensor essentially corresponds to displacement changes, which are relatively smooth. Some details changes in acceleration or velocity are difficult to identify in the displacement change information. For example, the velocity gradually increases from zero to a certain peak value, and then gradually decreases from the peak value to zero; the velocity change curve forms a waveform that first rises and then drops, while the displacement change curve presents only an ascending waveform. Therefore, compared to the signal component corresponding to the displacement, the peak-to-valley time width of the signal component corresponding to the velocity and acceleration is narrower, which may be called high-frequency component information. The high-frequency component extraction method can comprise performing polynomial fitting and smoothing filtering, and can also comprise performing differentiation processing on hemodynamic related information to generate high-frequency component information. For example, S1031 may specifically be: performing first-order differential processing on hemodynamic related information to generate first high-frequency component information, and performing second-order differential processing to generate second high-frequency component information. Vibration energy information can be generated by calculating the energy integral of the displacement change information point by point in a specified time window. A time width of the time window for energy integral can be 10 ms, 50 ms, 100 ms or other suitable widths, and the energy integral can be an absolute value, a square, a square root, or other calculation methods after taking the average value.

In addition, the vibration information acquired by the acceleration sensor essentially corresponds to hemodynamic acceleration change information, that is, the second high-frequency component information. At this time, the acceleration change information can be processed by first-order integration to generate the first high-frequency component information Vibration energy information can be obtained by integrating vibration information corresponding to acceleration.

Other types of sensors, such as radar sensors, if essentially sense the changes in vibration displacement of the subject, those of ordinary skill in the art can understand that, the signal processing method can use the above-mentioned signal processing process of the fiber-optic sensor, which is also within the protection scope of the present invention.

In the present invention, the first high-frequency component information and the second high-frequency component information are obtained by performing first-order differential processing and second-order differential processing on the displacement vibration information. It should be understood that, signals obtained using other methods such as polynomial fitting and smoothing filtering, which is equivalent to the first high-frequency component information and the second high-frequency component information after the first-order differential processing and the second-order differential processing, are also within the protection scope of the present invention.

Figure 4:
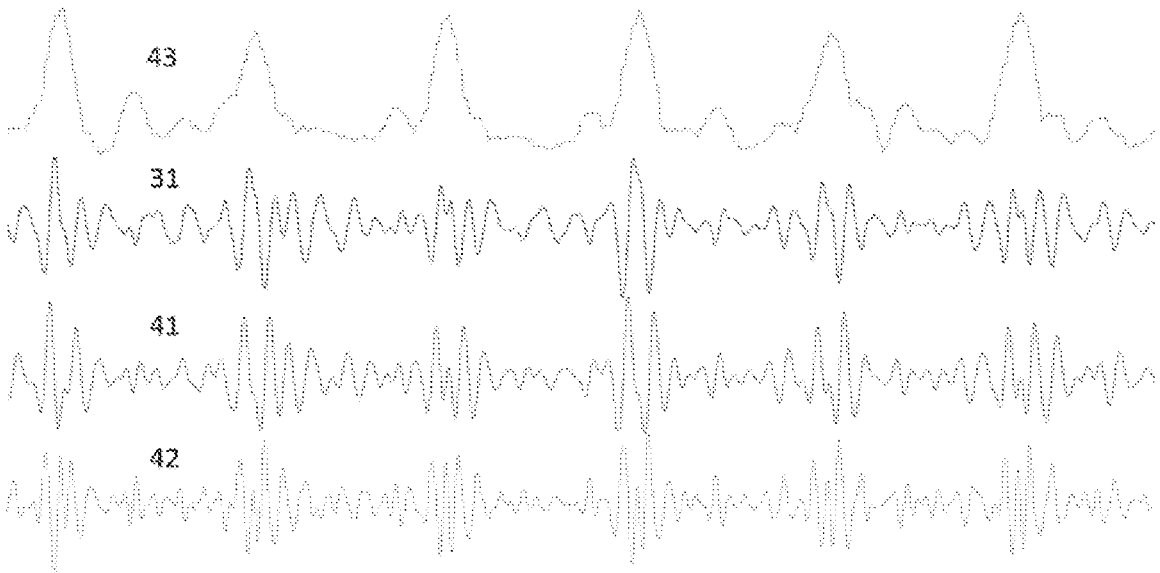
FIG. 4 is a diagram of time-domain waveforms of the hemodynamic related information, first high-frequency component information, and second high-frequency component information which are located on the same time axis.

As shown in FIG. 4, the curve 41 is the time-domain waveform curve of the first high-frequency component information, the curve 42 is the time-domain waveform curve of the second high-frequency component information, and the curve 43 is the vibration energy information curve. The horizontal axis represents time, and the vertical axis is dimensionless. Curve 41 and curve 42 are waveform curves obtained after performing first-order differential processing and second-order differential processing on the hemodynamic related information, namely the curve 31 of FIG. 3. The curve 43 is a waveform curve obtained by energy integration of the hemodynamic related information shown in FIG. 3. For comparison, the curve 31, the curve 41, the curve 42, and the curve 43 are placed on the same time axis for synchronous display.

S1032: synchronizing the hemodynamic related information, the first high-frequency component information, the second high-frequency component information, and the vibration energy information on the same time axis, and performing heartbeat segmentation.

In some examples, when the vibration information is continuously acquired, the hemodynamic related information, the first high-frequency component information, the second high-frequency component information, and the vibration energy information generated by processing the vibration information are also continuous data, thereby heartbeat segmentation is needed. The heartbeat segmentation can be performed based on the repetitive characteristics in the waveforms of: hemodynamic related information, the first high-frequency component information, or the second high-frequency component information. Since the heart activity has obvious periodicity, there are some obvious characteristics that have high repetitiveness. For example, the cardiac cycle of a normal person is between 0.6 s and 1 s, a search interval can be set accordingly, then search for the highest peak, and use the highest peak as a heartbeat segmentation feature. Similarly, the lowest valley can also be used as a heartbeat segmentation feature.

While obtaining the vibration information of the subject, the ECG information can be obtained through the ECG sensor. Because the ECG signal has low noise and clean signals, can be used for heartbeat segmentation with high accuracy. Therefore, the hemodynamic-related information, the first high-frequency component information or the second high-frequency component information can be segmented into heartbeats based on the ECG signals obtained synchronously with the vibration information.

In other examples, when the vibration information is obtained discretely in units of a cardiac cycle, heartbeat segmentation is not required, and S1032 can be omitted. In the first embodiment of the present invention, a subsequent processing can comprise: processing the hemodynamic related information, the first high-frequency component information, and the second high-frequency component information in each heartbeat. The subsequent processing can also comprise: performing data superposition and average on the hemodynamic related information, the first high-frequency component information, or the second high-frequency component information within a preset period (for example, 5 minutes or 30 minutes) according to the heartbeats to obtain the corresponding average information, and then performing a subsequent processing on the average information. Therefore, the hemodynamic related information, the first high-frequency component information, and the second high-frequency component information described below can refer to the data in a heartbeat, or the superposition and average data within a preset period according to the heartbeats.

S1033: performing wave group division on the hemodynamic related information, the first high-frequency component information, or the second high-frequency component information; and determining a first wave group, a second wave group, and a third wave group.

Figure 5:
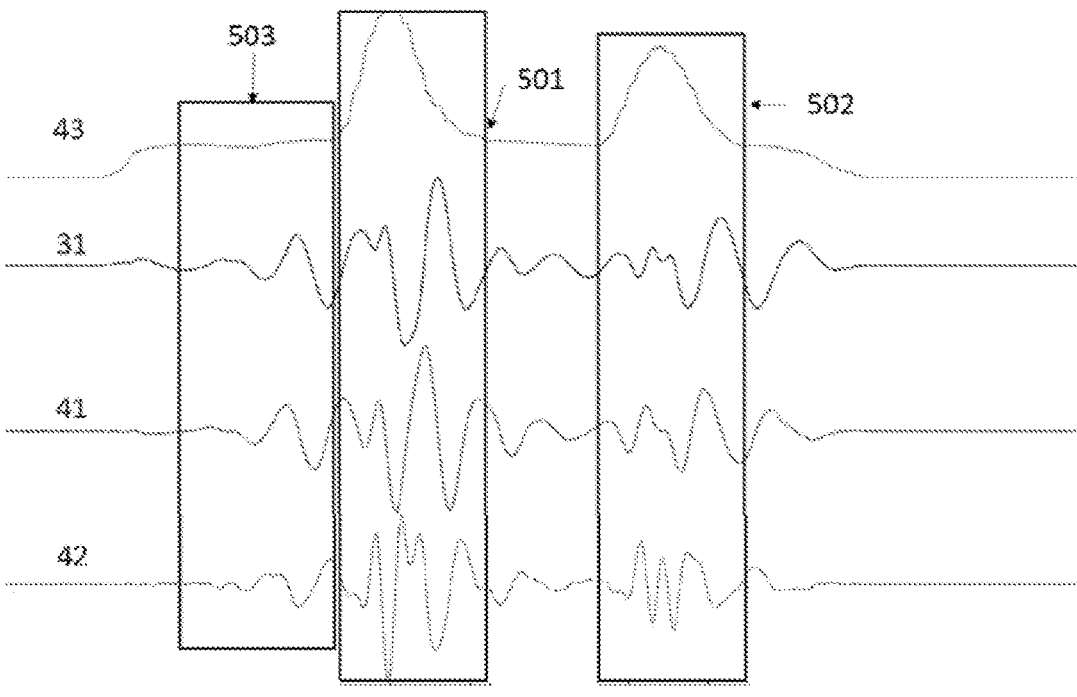
FIG. 5 is a diagram of a first wave group, a second wave group, and a third wave group of hemodynamic related information, vibration energy information, first high-frequency component information, and second high-frequency component information in a cardiac cycle.

The wave group division method can obtain the first wave group, the second wave group, and the third wave group according to the hemodynamic related information and the vibration energy information and based on the vibration energy information. FIG. 5 illustrates an enlarged view of the waveform of a cardiac cycle selected in FIG. 4. There are two energy envelopes in the vibration energy information 43. One energy envelope has a relatively high energy peak and its duration window includes the time corresponding to the highest peak of the hemodynamic related information, which is determined as the systolic energy envelope, while the other energy envelope is diastolic energy envelope. The duration of the systolic energy envelope is used as a first-time window, and the duration of the diastolic energy envelope is used as a second time window. Determining the wave clusters on the hemodynamic information, the first high-frequency component information, and the second high-frequency component information which are synchronized with the vibration energy information, corresponding to the first time window, as the respective first wave groups; while corresponding to the second time window, as the respective second wave groups; and further, determining the "W"-shaped wave groups before the respective first wave groups as the respective third wave groups. Because of the synchronization in time, for comparison, the first wave groups on the curve 31, the curve 41, and the curve 42 are represented as 501, the second wave groups are represented as 502, and the third wave groups are represented as 503. It should be understood that each of the curve 31, the curve 41, and the curve 42 can all be divided into the first wave group, the second wave group, and the third wave group.

Figure 6:
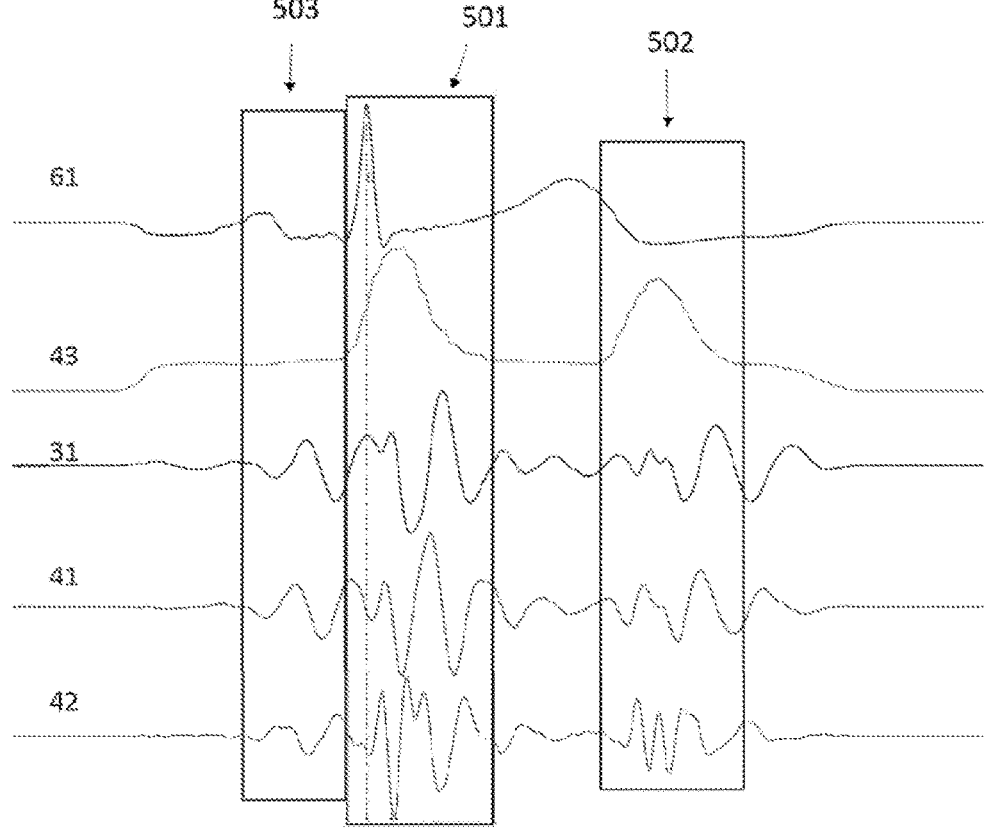
FIG. 6 is a diagram of time-domain waveforms of electrocardiographic information, hemodynamic related information, vibration energy information, first high-frequency component information, and second high-frequency component information on the same time axis in a cardiac cycle.

In some examples, the wave group division can also be: obtaining the vibration information of the subject and synchronously obtaining ECG information through an ECG sensor; where the ECG information can be used to distinguish between the systolic energy envelope and the diastolic energy envelope, and QRS complex of the ECG information is closest to the systolic energy envelope of the vibration energy information; therefore, the first wave groups, the second wave groups and the third wave groups can be divided by the ECG information. As shown in FIG. 6, the synchronously acquired ECG information is synchronized with the curves in FIG. 5 on the same time axis, where the curve 61 is the ECG information. Since the ECG information represents the electrophysiological activity of the heart, and electrophysiological activity has a strong correlation with the mechanical vibration of the heart, so it can be used for verification with vibration information.

S1034: determining a first parameter and a second parameter based on the second wave group and the third wave group of the hemodynamic related information, the first high-frequency component information, or the second high-frequency component information.

In the first embodiment of the present invention, S1034 can be implemented by the following two methods.

First Method

Figure 7A:
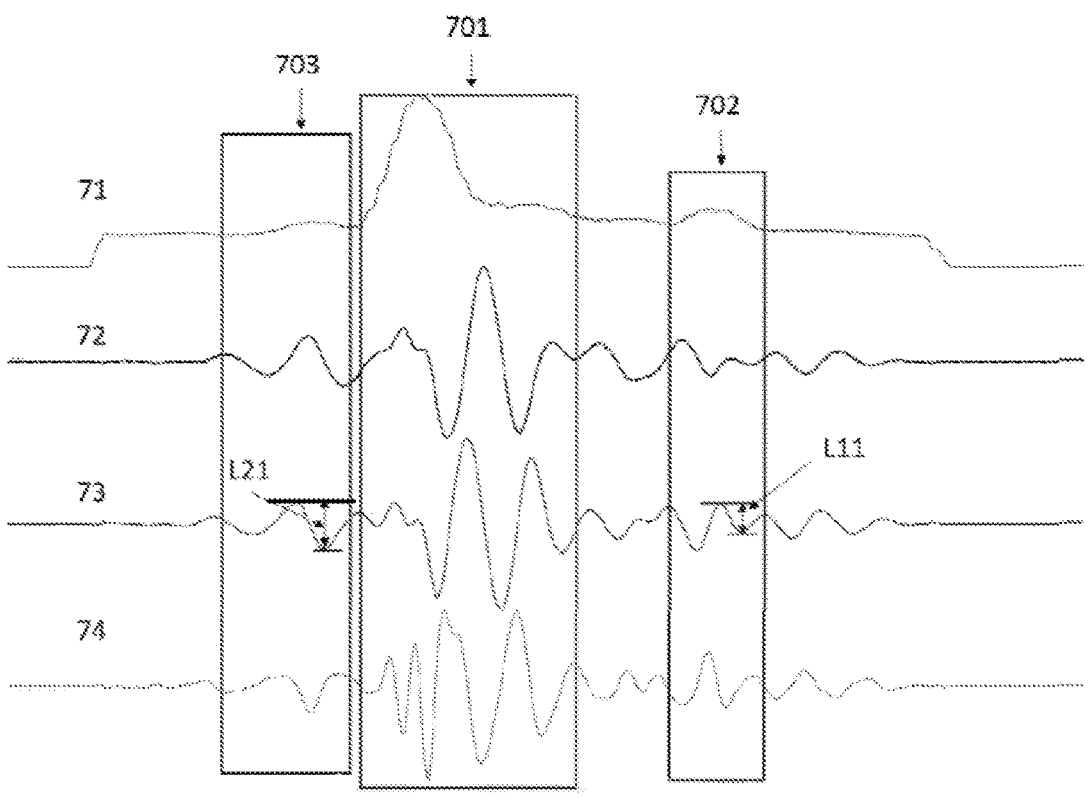
FIGS. 7A and 7B are diagrams of the values of the first parameter and the second parameter based on the vibration information of the subject B.
Figure 7B:
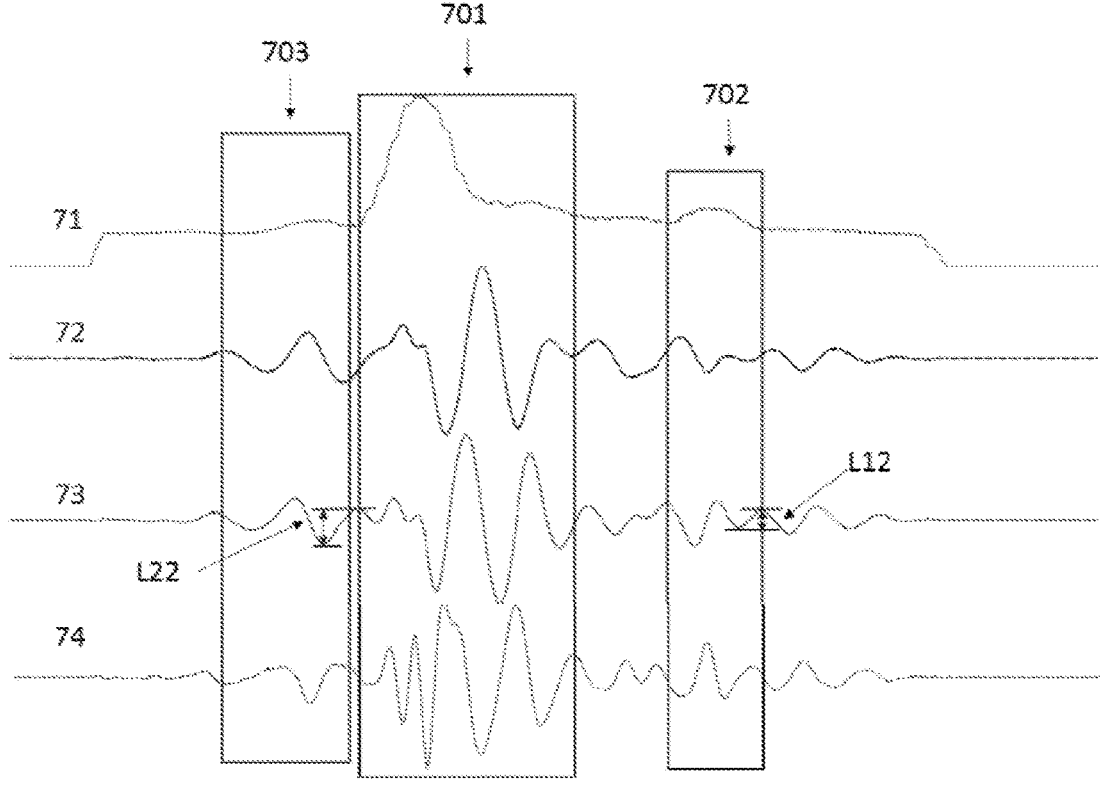

In an exemplary embodiment, performing a waveform search based on the second wave group and the third wave group on the first high-frequency component information curve; and determining a first parameter and a second parameter, specifically comprises steps of:

first, performing a "W" waveform search on the second wave group of the first high-frequency component information; and determining a first parameter as the amplitude between the second wave trough and the first wave peak before it in the "W" waveform. As shown in FIG. 7A, the height L11 is the first parameter. The amplitude between the second wave trough and the first wave peak after it in the "W" waveform can also be used as the first parameter. As shown in FIG. 7B, the height L12 is the first parameter. Where the curves shown in FIGS. 7A and 7B are generated based on the vibration information corresponding to the thoracic cavity of the subject B, the curve 72 represents hemodynamic related information; the curve 71 represents the vibration energy information, which is obtained after the energy integration of the curve 72; the curve 73 is the time-domain waveform curve of the first high-frequency component information, the curve 74 is the time-domain waveform curve of the second high-frequency component information, and the curve 73 and the curve 74 are the waveform curves of the curve 72 after first-order differential processing and second-order differential processing.

Figure 7C:
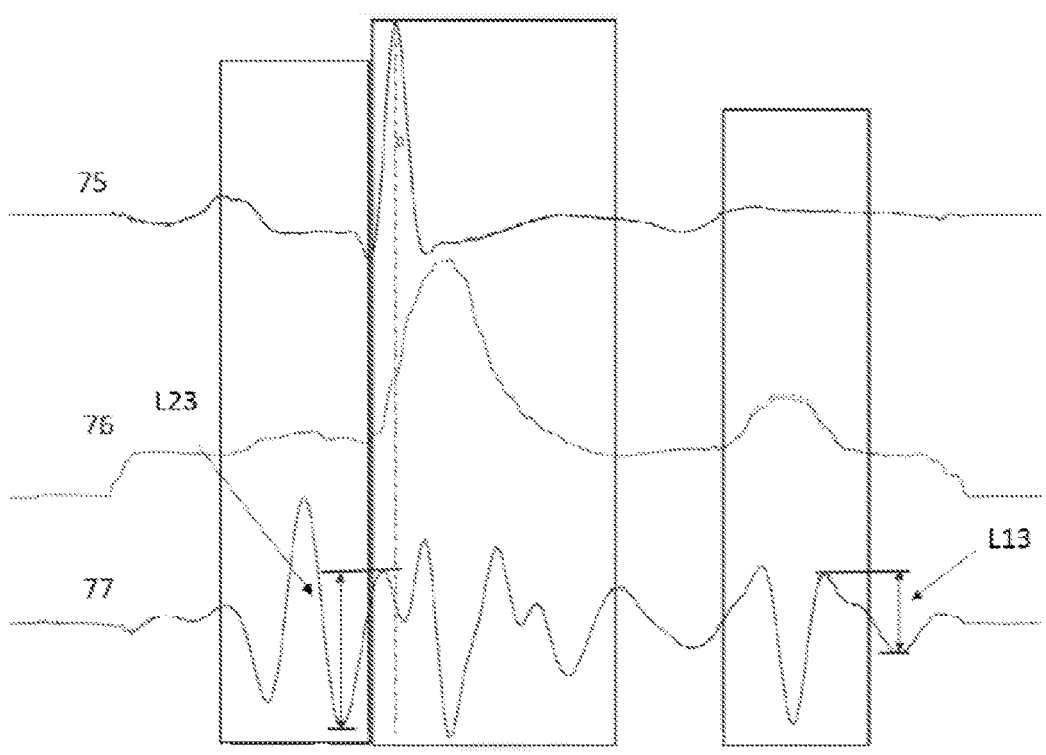
FIG. 7C is a diagram of the values of the first parameter and the second parameter based on the vibration information of the subject C.

In addition, in some embodiments, when performing a "W" waveform search on the second wave group of the first high-frequency component information, if the "W" waveform is not all included in the second wave group, that is, it is beyond the range of the second wave group, then performing a "W" waveform search from the start of the second wave group and determining the first "W" waveform as a target "W" wave form. If the second wave trough of the "W" waveform is not flat, such as has inflection points or bumps, then determining the deepest wave trough as the second wave trough of the "W" waveform. As shown in FIG. 7C, each curve is generated based on the vibration information on a body surface corresponding to the thoracic cavity of the subject C. Where the curve 75 represents the ECG information acquired synchronously, the curve 76 represents the vibration energy information, and the curve 77 represents the first high-frequency component information. Here, the height L13 is used as the first parameter.

Secondly, in the same cardiac cycle, performing a "W" waveform search on the third wave group of the first high-frequency component information, and determining a second parameter as the amplitude between the second wave trough and the first wave peak before it in the "W" waveform. As shown in FIG. 7A, the height L21 is the second parameter. The amplitude between the second wave trough and the first wave peak after it in the "W" waveform can also be used as the second parameter. As shown in FIG. 7B, the height L22 is the first parameter.

In some embodiments, when performing a "W" waveform search on the third wave group of the first high-frequency component information, if a position of the "W" waveform is uncertain, the ECG information and the first high-frequency component information acquired in synchronization with the vibration information can be synchronized on the same time axis as a reference; and the "W" waveform is usually in the PR interval of the ECG information. If the "W" waveform is beyond a range of the third wave group, then determining a complete "W" waveform as a target "W" waveform. The amplitude between the second wave trough and the first wave peak after it in the "W" waveform is the second parameter. As shown in FIG. 7C, the height L23 is the second parameter.

It should be understood that the above description is based on an example in which the first parameter and the second parameter are determined based on the second wave group and the third wave group on the first high-frequency component information. The above method is also applicable to the hemodynamic related information or the second high-frequency component information.

Second Method

Figure 8A:
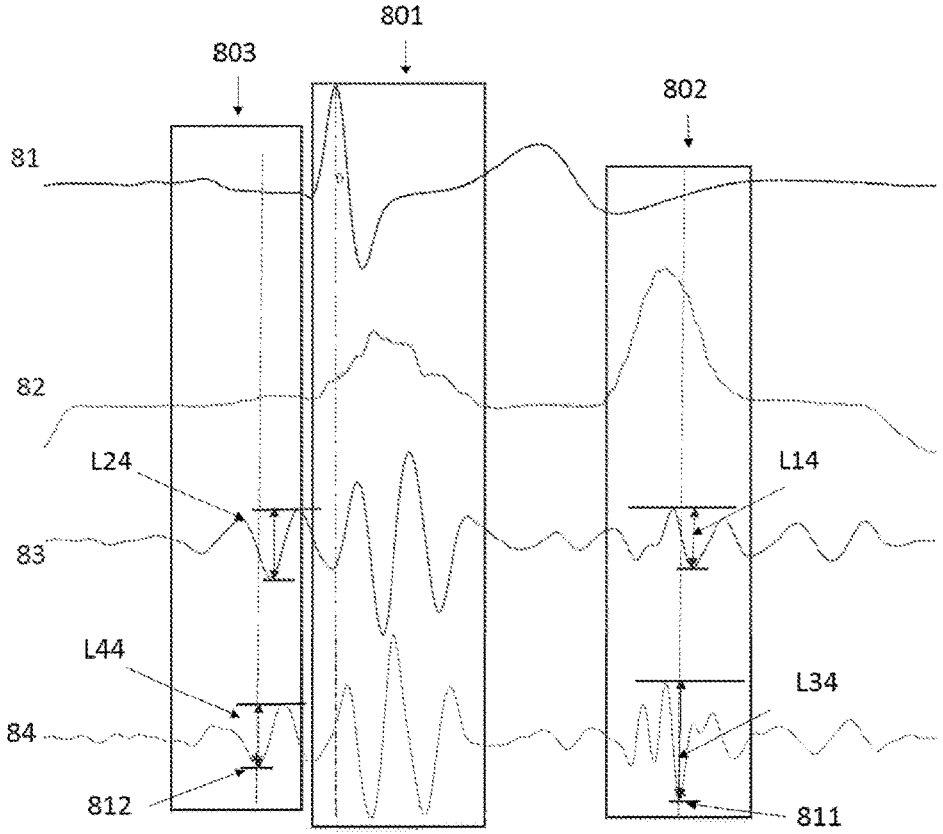
FIGS. 8A and 8B are diagrams of the values of the first parameter and the second parameter based on the vibration information of the subject D.
Figures 8B, 9A:
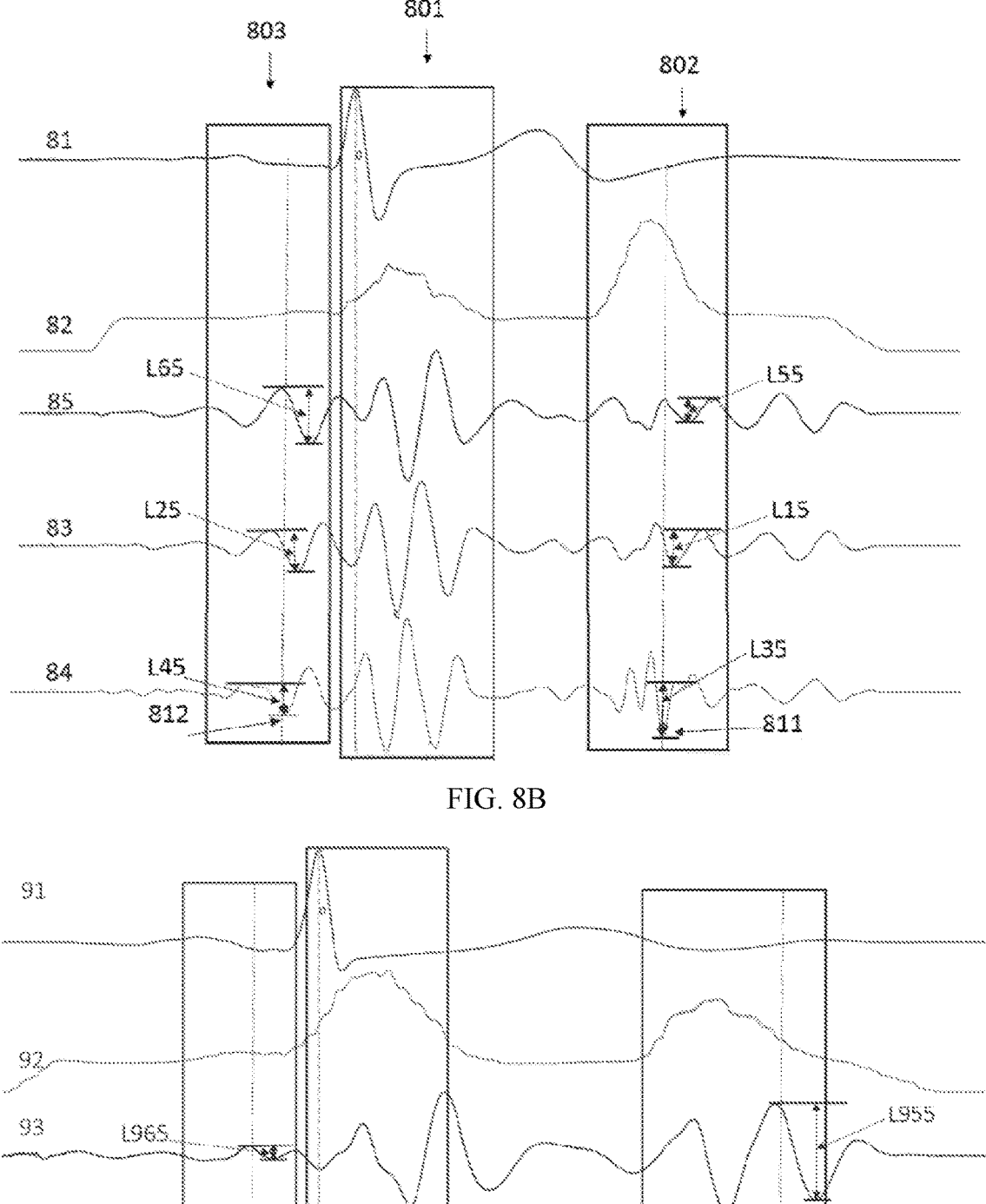
FIG. 9A is a diagram of the values of the first parameter and the second parameter based on the vibration information of the subject E.

In some examples, if a position of the "W" waveform is difficult to determine, determining a first characteristic point and a second characteristic point based on the second wave group and the third wave group of the second high-frequency component information; and then determining a first parameter and a second parameter of the hemodynamic information, the first high-frequency component information or the second high-frequency component information based on the first characteristic point and the second characteristic point; the second method specifically comprises steps of:

a first step: determining a first characteristic point and a second characteristic point based on the second wave group and the third wave group of the second high-frequency component information; specifically comprising:

first, determining a first characteristic point as a first wave trough after the highest peak of the second wave group of the second high-frequency component information, as shown in FIG. 8A, where the point 811 is the first characteristic point;

secondly, performing a wave trough search on the third wave group of the second high-frequency component information, and determining a second characteristic point as the second trough, as shown in FIG. 8A, where the point 812 is the second characteristic point;

where the curves shown in FIGS. 8A and 8B are generated based on the vibration information on a body surface corresponding to the thoracic cavity of the subject D, the curve 85 represents hemodynamic related information, and the curve 82 represents the vibration energy information, which is obtained after energy integration of the curve 85; the curve 83 is the time-domain waveform curve of the first high-frequency component information, the curve 84 is the time-domain waveform curve of the second high-frequency component information, the curve 83 and the curve 84 are the waveform curves of curve 85 after first-order differential processing and second-order differential processing; and the curve 81 represents the ECG information acquired synchronously;

a second step: determining a first parameter and a second parameter of the hemodynamic information, the first high-frequency component information or the second high-frequency component information based on the first characteristic point and the second characteristic point; specifically comprising:

determining a first parameter of the second high-frequency component as the amplitude between the wave trough where the first characteristic point is located and the first wave peak before it on the second high-frequency component information, as shown in FIG. 8A, where the height L34 is the first parameter of the second high-frequency component; in FIG. 8A, the horizontal axis represents time, and the vertical axis is dimensionless; the height L34 refers to the amplitude between the wave trough where the first characteristic point is located and the first wave peak before it; the first parameter of the second high-frequency component may also be the amplitude between the wave trough where the first characteristic point is located and the first wave peak thereafter, as shown in FIG. 8B, where the height L35 is the first parameter of the second high-frequency component;

in the same cardiac cycle, determining a second parameter of the second high-frequency component as the amplitude between the wave trough corresponding to the second characteristic point and the first wave peak thereafter on the second high-frequency component information, as shown in FIG. 8A, where the height L44 is the second parameter; the amplitude between the wave trough where the second characteristic point is located and the first wave peak before it can also be used as the second parameter of the second high-frequency component, as shown in FIG. 8B, where the height L45 is the second parameter of the second high-frequency component;

determining the first parameter and the second parameter of the first high-frequency component information or the hemodynamic related information based on the first characteristic point and the second characteristic point using other similar methods, e.g.:

determining a first parameter of the first high-frequency component as the amplitude between the first wave trough after the corresponding time point of the first characteristic point and the first wave peak before it on the first high-frequency component information, as shown in FIG. 8A, where the height L14 is the first parameter of the first high-frequency component; the first parameter of the first high-frequency component may also be the amplitude between the first wave trough after the corresponding time point of the first characteristic point and the first wave peak thereafter, as shown in FIG. 8B, where the height L15 is the first parameter of the first high-frequency component;

in the same cardiac cycle, determining a second parameter of the first high-frequency component as the amplitude between the first wave trough after the time point corresponding to the second characteristic point and the first wave peak thereafter on the first high-frequency component information, as shown in FIG. 8A, where the height L24 is the second parameter of the first high-frequency component; the amplitude between the first wave trough after the corresponding time point of the second characteristic point and the first wave peak before it may also be used as the second parameter of the first high-frequency component, as shown in FIG. 8B, where the height L25 is the second parameter of the first high-frequency component.

The above methods are also applicable to hemodynamic related information. Determining a first parameter of the hemodynamic related information as the amplitude between the first wave trough after the corresponding time point of the first characteristic point and the first wave peak thereafter on the hemodynamic related information. As shown in FIG. 8B, the height L55 is the first parameter of the first high-frequency component. In the same cardiac cycle, on the hemodynamic related information, the amplitude between the first wave trough after the corresponding time point of the second characteristic point and the first wave peak before it can also be determined as the first parameter of the hemodynamic related information. As shown in FIG. 8B, the height L65 is the second parameter of the first high-frequency component.

A ventricular filling event during early ventricular diastole comprises an acceleration event of transvalvular blood flow and a deceleration event of transvalvular blood flow during early ventricular diastole. Transvalvular blood flow mainly refers to the blood flow from the left atrium into the left ventricle through the mitral valve.

The ventricular filling event during early ventricular diastole and the atrial systole event during late ventricular diastole, can obtain information of different dimensions through different sensors. For example, the electrophysiological sensor can obtain the electrical signal of the event, and the vibration sensor can obtain the vibration signal of the event. Specifically, body surface motion corresponding to a subject's thoracic cavity can be acquired through the vibration sensor, and then the ventricular filling event during early ventricular diastole and the atrial systole event during late ventricular diastole of the subject can be extracted therefrom. The ventricular filling event during early ventricular diastole comprises the vibration formed on the body surface of the subject by muscle movement and blood flow movement caused by the ventricular filling; and the atrial systole event during late ventricular diastole comprises the vibration formed on the body surface of the subject by muscle movement and blood flow movement caused by the atrial systole. In the first embodiment of the present invention, the first parameter is used to represent the vibration amplitude formed on the body surface of the subject by muscle movement and blood flow movement caused by the ventricular filling during early ventricular diastole; and the second parameter is used to represent the vibration amplitude formed on the body surface of the subject by muscle movement and blood flow movement caused by the atrial systole during late ventricular diastole. It is understandable that in addition to vibration amplitude, parameters such as vibration energy, vibration frequency, or vibration time, can also be used to represent the ventricular filling event during early ventricular diastole and the atrial systole event during late ventricular diastole.

Referring to FIGS. 7 and 8, when the first parameter is the falling edge amplitude between the second wave trough or the first characteristic point and the first wave peak before it in the "W" waveform of the second wave group of the first high-frequency component information, it can be used to represent the vibration amplitude formed on the body surface by muscle movement and blood flow movement which are caused by the acceleration event of transvalvular blood flow during early ventricular diastole, such as L11, L14, L34. When the first parameter is the rising edge amplitude between the second wave trough or the first characteristic point and the first wave peak thereafter in the "W" waveform of the second wave group in the first high-frequency component information, it can be used to represent the vibration amplitude formed on the body surface by muscle movement and blood flow movement which are caused by the deceleration event of transvalvular blood flow during early ventricular diastole, such as L12, L55, L15, L35. The two values of the second parameter are both used to represent the vibrations formed on the body surface by muscle movement and blood flow movement which are caused by atrial systole, such as L24, L25, L44, and L45.

S104: generating an indicating parameter on the basis of the first parameter and of the second parameter; and assessing a ventricular filling pressure of the subject based on the indicating parameter. For example, a ratio of the first parameter to the second parameter can be used as the indicating parameter. The indicating parameter obtained on the first high-frequency component information can be used as the indicating parameter I1, the indicating parameter obtained on the second high-frequency component information can be used as the indicating parameter I2, and the indicating parameter obtained on the hemodynamic information is used as the indicating parameter I3. For example, the indicating parameter I1=L12/L22, the indicating parameter I2=L35/ L45, the indicating parameter I3=L55/L65. When the indicating parameter is greater than a threshold, it is determined that the subject's diastolic function is in an elevated filling pressure state. Where the elevated filling pressure state can be identified when ultrasound parameters: E/e'>14, Vtr>2.8 m/s, and E/A>1. At this time, the heart is in a state of restrictive filling, ventricular relaxation is impaired and ventricular compliance is reduced. An elevated filling pressure will cause the heart into a rapid vicious circle, and timely intervention is required to avoid further deterioration.

FIG. 9A is a diagram of the first parameter and the second parameter calculated based on the vibration information of the thoracic body surface of the subject E. The subject E is a patient with heart failure in a state of evaluated filling pressure. Where the curve 91 represents the ECG information obtained synchronously with the vibration information, the curve 93 is the time-domain waveform diagram of hemodynamic related information, and the curve 92 is the time-domain waveform diagram of the vibration energy information, which is obtained after the energy integration of the curve 93, the curve 94 is the time-domain waveform curve of the first high-frequency component information, the curve 95 is the time-domain waveform curve of the second high-frequency component information, and the curve 94 and the curve 95 are the waveform curves of curve 93 after first-order differential processing and second-order differential processing. The first parameters can be L955, L915, L935, and the second parameter can be L965, L925, L915. Compared with FIG. 7 and FIG. 8, the first parameters of the patients with heart failure have great changes. Here, a ratio of the first parameter and the second parameter is used to represent the change.

A person of ordinary skill in the art can obtain a method for evaluating the diastolic function when a ratio of the second parameter to the first parameter is used as the indicating parameter, which is also included in the protection scope of the present invention. In addition, those of ordinary skill in the art can easily obtain that performing other calculations on the second parameter and the first parameter to generate the indicating parameter, including but not limited to: addition, subtraction, multiplication, division, exponent, etc., which are also all within the protection scope of the present invention.

Figure 9B:
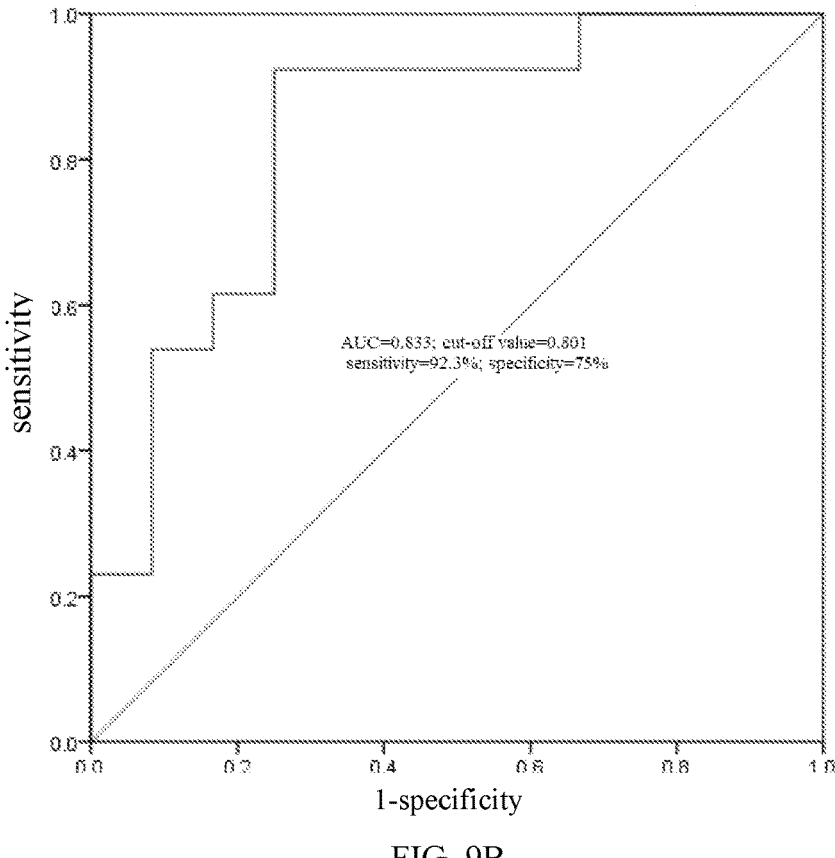
FIGS. 9B, 9C, and 9D are ROC curves of indicating parameters.
Figure 9C:
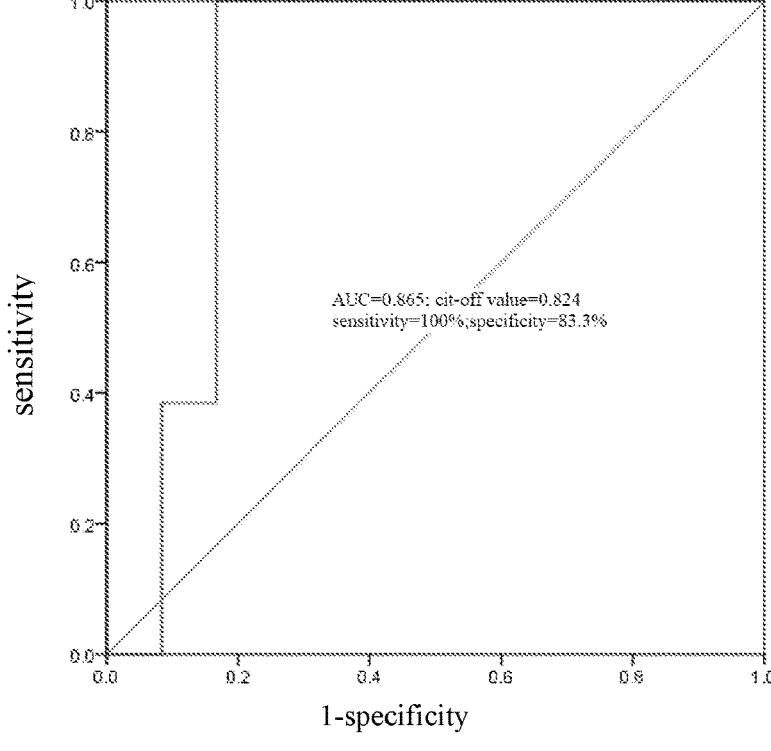
Figures 9D, 10:
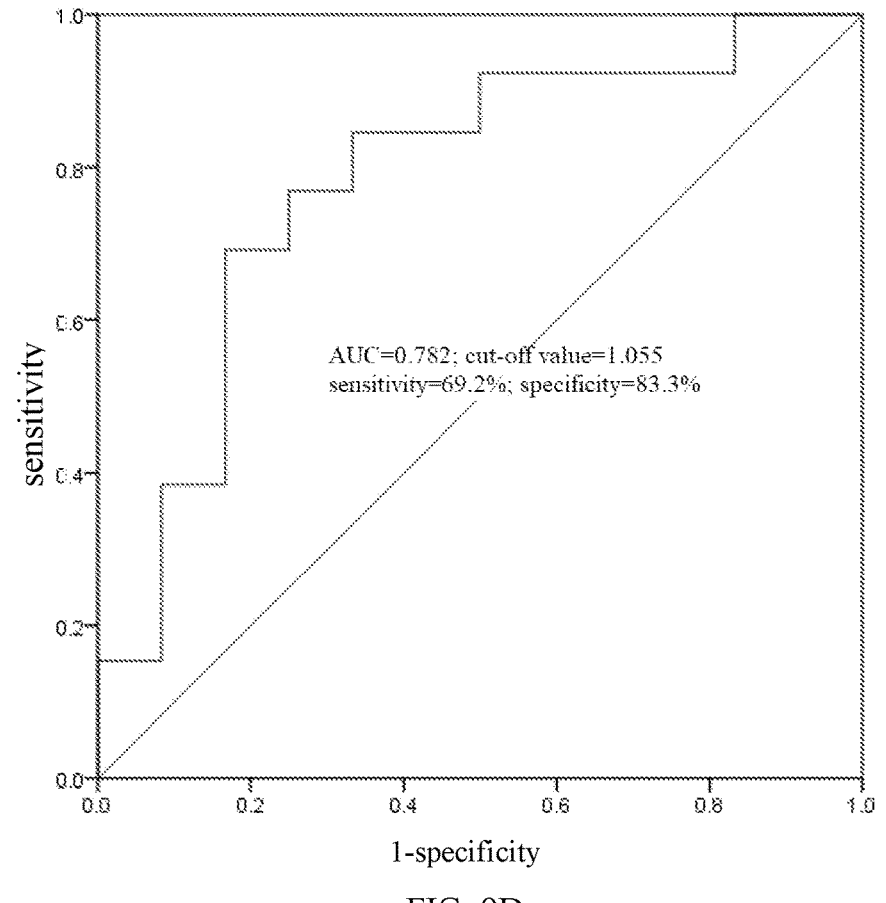
FIG. 10 is a block diagram of a diastolic function assessment device according to the third embodiment of the present invention.

Twenty-five heart failure patients as testing subjects were enrolled in a clinical study, where twelve patients with elevated filling pressure (marked as positive) and thirteen patients without elevated filling pressure (marked as negative). According to the above-mentioned diastolic function assessment method 100, calculates indicating parameters of the twenty-five subjects. Analyze sensitivity and specificity of the indicating parameters for the twenty-five subjects, and construct the ROC curves as shown in FIGS. 9B, 9C, and 9D, which are the ROC curves based on indicating parameter I1, indicating parameter I2 and indicating parameter I3. Based on the indicating parameter I1, an assessment result of ventricular filling pressure is that: the AUC area is 0.833, the optimal cut-off value is 0.801; the sensitivity is 92.3%, and the specificity is 75%. Based on the indicating parameter I2, an assessment result of ventricular filling pressure is that: AUC area is 0.865, the optimal cut-off value is 0.824; the sensitivity is 100%, and the specificity is 83.3%. Based on the indicating parameter I3, an assessment result of ventricular filling pressure is that: the AUC area is 0.782, the optimal cut-off value is 1.055; the sensitivity is 69.2%, and the specificity is 83.3%. The threshold is determined based on people with heart failure. In some embodiments of the present invention, the threshold may also be an absolute threshold, which is used to distinguish between healthy people and people with cardiac diastolic dysfunction. The threshold may also depend on the subject itself, for example, a relative threshold when diastolic function deteriorates can be obtained on the basis of the analysis of personal history data of the monitored subject.

In the first embodiment of the present invention, the diastolic function is represented by ventricular filling pressure, for example, an elevated filling pressure represents serious diastolic dysfunction. In addition, the diastolic function can also be represented by atrial pressure. The left ventricular filling pressure is related to the left atrial pressure and the pulmonary artery pressure due to the heart structure. Therefore, in some embodiments, the indicating parameters can be used to assess the filling pressure; the indicating parameters after a series of transformation calculation, can also be used to indirectly assess the left atrial pressure, the pulmonary artery pressure, and the degree of heart failure, etc., which are also within the protection scope of the present invention.

Second Embodiment

The second embodiment of the present invention provides a computer readable storage medium having computer programs stored thereon, which when being executed by a processor, cause the processor to perform the steps of the diastolic function assessment method of the present invention in the first embodiment.

Third Embodiment

The third embodiment of the present invention provides a diastolic function assessment device. FIG. 10 illustrates a block diagram of a diastolic function assessment device 200. The diastolic function assessment device 200 may be a special computer device to process the vibration information acquired by a fiber-optic sensor.

For example, the diastolic function assessment device 200 may comprise a communication port 201 connected to a network for data communication. The diastolic function assessment device 200 may further comprise one or more processors 203 for executing computer instructions. The computer instructions may comprise, for example, routines, programs, objects, components, data structures, procedures, modules, and functions that perform the ventricular filling pressure assessment method described herein. For example, the processor 203 can obtain the vibration information of the fiber-optic sensor, and preprocess the vibration information to generate hemodynamic related information.

In some examples, the processors 203 may comprise one or more hardware processors, such as: a microcontroller, a microprocessor, a Reduced Instruction Set Computer (RISC), an Application Specific Integrated Circuit (ASIC), a Graphics Processing Unit (GPU)), Central Processing Unit (CPU), Digital Signal Processor (DSP), Field Programmable Gate Array (FPGA), Advanced RISC Machine (ARM), and Programmable Logic Device (PLD) etc., or any circuit or processor or a combination thereof capable of performing one or more functions.

The diastolic function assessment device 200 may comprise an internal communication bus 205, a memory 207 for various data processed and/or sent by the computer, and program instructions stored in other types of non-transitory storage media executed by the processor 203 in the memory 207. The method and/or process of the present invention can be implemented by program instructions. The diastolic function assessment device 200 also comprises an input/output component 209, which is used for input/output between the computer and other components (for example, User Interface Elements).

For ease of description, only one processor is described in the diastolic function assessment device 200 of the present invention. However, it should be noted that the diastolic function assessment device 200 of the present invention may also comprise multiple processors. Therefore, the process and/or method disclosed in the present invention may be executed by one processor as described in the present invention, and can also be executed jointly by multiple processors. For example, if the processor 203 of the diastolic function assessment device 200 in the present invention performs step A and step B, it should be understood that step A and step B can also be performed jointly or separately by two different processors (For example, a first processor executes step A, a second processor executes step B, or the first and second processors jointly execute steps A and B).

Fourth Embodiment

The fourth embodiment of the present invention provides a diastolic function assessment system, including:

one or more vibration sensors; and a ventricular filling pressure assessment device provided in the third embodiment of the present invention.

Figure 11:
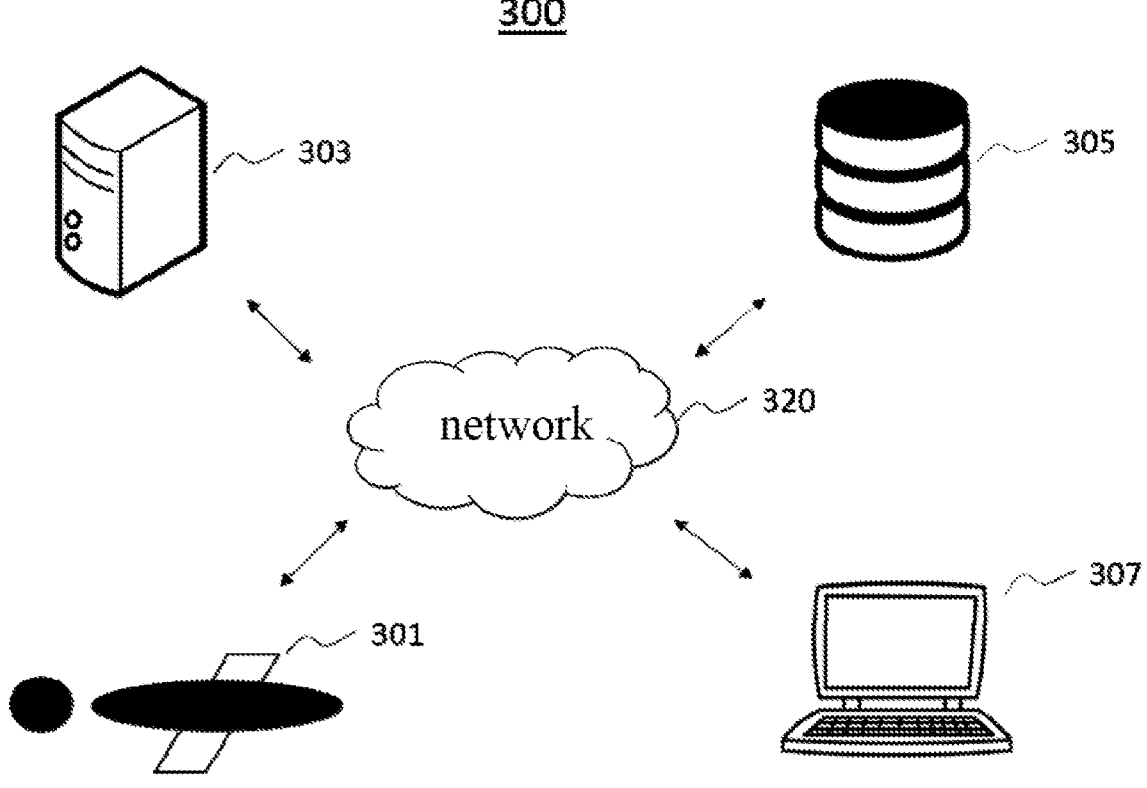
FIG. 11 is a block diagram of a system for monitoring a ventricular filling pressure in accordance with a fourth embodiment of the present invention.

FIG. 11 illustrates a block diagram of a ventricular filling pressure monitoring system 300, which may comprise one or more vibration sensors 301, one or more diastolic function assessment devices 303, and one or more storage devices 305.

Wherein, the vibration sensor 301 may be an acceleration sensor, a speed sensor, a displacement sensor, a pressure sensor, a strain sensor, or a stress sensor; and it may also be a sensor which converts physical quantities equivalently based on acceleration, speed, displacement, or pressure (such as electrostatic charge sensors, inflatable pressure sensors, radar sensors, etc.). The strain sensor can be a fiber-optic sensor. When the vibration sensor 301 is a fiber-optic sensor, it can be placed under the subject's body. For example, the subject can be in a posture such as supine, prone, side-lying, etc. The fiber-optic sensor can be placed on the bed, and the subject is supine (prone or side-lying) on it. Taking the subject in a supine position as an example, the preferable measurement position is that the fiber-optic sensor is placed under the subject's back, and preferably, the fiber-optic sensor is placed in the area corresponding to the body surface between the subject's left and right shoulder blades. For ease of description, the body surface between the left and right shoulder blades of the subject is defined as the middle shoulder. Those of ordinary skill in the art can understand that when the subject lies in the prone position, the subject's chest is the measurement position corresponding to the back of the subject in the supine position. In addition, the vibration sensor can also be placed on the contact surface behind the back of the subject in the supine posture at a certain tilt angle or on the contact surface behind the back of the subject leaning on a wheelchair or other leaning objects to acquire the vibration information.

The diastolic function assessment device 303 is as described in the third embodiment of the present invention, may be connected to the vibration sensor 301 through the network 320. The network 320 may be a single network, such as a wired network or a wireless network, or a combination of multiple networks. The network 320 may comprise, but is not limited to, a Local Area Network, a Wide Area Network, a shared internet, a dedicated internet, and the like. The network 320 may comprise a variety of network access points, such as wireless or wired access points, base stations, or network access points, through which other components of the ventricular filling pressure monitoring system 300 can connect to the network 320 and transmit information through the network.

The storage device 305 may be configured to store data and instructions. The storage device 305 may comprise, but is not limited to, Random Access Memory, Read Only Memory, Programmable Read Only Memory, and the like. The storage device 305 may store information using electrical energy, magnetic energy, or optical methods, such as Hard Disks, Floppy Disks, Magnetic Core Memories, CDs, DVDs, and the like. The storage devices mentioned above are just a few examples, and the storage devices used by the storage device 305 are not limited to these.

In some examples, the ventricular filling pressure monitoring system 300 may further comprise an output device 307 is used to output the result of the diastolic function assessment, and the output methods comprise but are not limited to graphics, text, data, voice, etc., such as one or more of graphic display, digital display, voice broadcast, braille display, etc. The output device 307 may be one or more of a display, a mobile phone, a tablet computer, a projector, a wearable device (watch, earphone, glasses, etc.), a braille display, and the like. In some examples, the output device 307 can display the assessment result of the ventricular filling pressure of the subject 102 in real time. In other examples, the output device 307 can display a report in non-real time, which is the measurement result of the subject in a preset time period, for example, the user's ventricular filling pressure monitoring results during the sleeping time period. When monitoring a subject with heart failure, if a state of elevated filling pressure is assessed by the diastolic function assessment device, the subject with heart failure will face a worsening heart failure at this time and need to be hospitalized. The output device of the monitoring system can send reminders to the heart failure patient, such as sending text messages, emails, phone calls, WeChat, and other instant messages; and can also send a message to the family doctor of the heart failure patient, prompt that the patient may suffer from worsening heart failure to help doctors to make decisions. The system may further comprise a doctor-patient communication platform, and when the doctor receives the system notification that the patient may suffer from worsening heart failure, he can communicate with the patient in time.

For another example, the output device 307 can also implement an early warning, for example, a voice warning. When the diastolic function assessment device evaluates the diastolic function of the patient with heart failure being a state of elevated filling pressure, the patient with heart failure will suffer from worsening heart failure at this time, and the system can remind the patient to see a doctor in time by voice warning.

In the present invention, a method for monitoring the ventricular filling pressure by acquiring the vibration information of the subject without intruding the body, is a passively measuring, and can realize continuous monitoring. The subject only needs to lie on the measuring device to perform the measurement, and no need for professional assistance. The method has the advantages of high measurement accuracy and simple operation, can improve the comfort of the tester, and can be applied to scenes such as hospitals and homes. The ventricular filling pressure monitoring system provided in the present invention can evaluate the ventricular filling pressure of the subject, and then prompt a warning in advance when deterioration appear, so as to help the subject avoid deterioration.

A person of ordinary skill in the art can understand that all or part of the steps in the various methods of the above-mentioned embodiments can be completed by a program instructing relevant hardware. The program can be stored in a computer-readable storage medium. The computer-readable storage medium may comprise: ROM (Read Only Memory), RAM (Random Access Memory), magnetic disk or optical disk, etc.

The foregoing descriptions are only preferable embodiments of the present invention, and are not intended to limit the present invention. Any modification, equivalent replacement, and improvement made within the spirit and principle of the present invention shall be included in the protection scope of the present invention.

What is claimed is:

1. A cardiac diastolic function assessment method, performed by one or more processors executing one or more computer programs stored in a memory, comprising:

non-invasively and continuously acquiring vibration information on a body surface corresponding to a thoracic cavity of a supine subject using a fiber-optic sensor which is connected to the one or more processors, wherein the fiber-optic sensor is configured to be placed under the subject's body between a left shoulder blade and a right shoulder blade, a sense area of the fiber-optic sensor is at least 20 square centimeters and covers the body surface corresponding to the right shoulder blade of the subject;

preprocessing the vibration information to generate hemodynamic-related information within 9 Hz-45 Hz, comprising filtering, noise removal and signal scaling;

performing first-order differential processing on the hemodynamic-related information to generate first high-frequency component information;

performing energy integration on the hemodynamic-related information to generate vibration energy information, wherein the vibration energy information comprises two energy envelopes in one cardiac cycle, one energy envelope has a higher energy peak and is a systolic energy envelope with a duration as a first-time window, and the other energy envelope is a diastolic energy envelope with a duration as a second-time window, a highest peak of the hemodynamic related information in the same cardiac cycle of the two energy envelopes is located within the first-time window of the systolic energy envelope;

synchronizing the hemodynamic-related information, the first high-frequency component information, and the vibration energy information on a same time axis, and performing heartbeat segmentation;

determining, on the first high-frequency component information, in each cardiac cycle, wave clusters within the first-time window as a first wave group, wave clusters within the second time window as a second wave group, and "W"-shaped wave clusters before the first wave group as a third wave group;

determining a first parameter and a second parameter, comprising:

on the second wave group of the first high-frequency component information, performing a first "W" waveform search and determining the first parameter as a first amplitude between a second wave trough in the "W" waveform of the second wave group and a first wave peak of the second wave group before or after the second wave trough in the "W" waveform of the second wave group;

on the third wave group of the first high-frequency component information in the same cardiac cycle of the second wave group, performing a second "W" waveform search and determining the second parameter as a second amplitude between a second wave trough in the "W" waveform of the third wave group and a first wave peak of the third wave group before or after the second wave trough in the "W" waveform of the third wave group;

wherein the first parameter comprises a vibration amplitude formed on the body surface of the subject by muscle movement and blood flow movement caused by ventricular filling during early ventricular diastole; and the second parameter comprises the vibration amplitude formed on the body surface of the subject by the muscle movement and the blood flow movement caused by atrial systole during late ventricular diastole; and determining an indicating parameter $I_1$, which is a ratio of the first parameter to the second parameter, and determining the subject to be in an elevated filling pressure if the indicating parameter $I_1$ is greater than a threshold; wherein the threshold depends on a certain population.

2. The method of claim 1, wherein the performing heartbeat segmentation comprises:

performing, on the hemodynamic related information or the first high-frequency component information, a search for the highest peak or a lowest valley with a search interval between 0.6 s and 1 s; and performing heartbeat segmentation based on the searched highest peak or the lowest valley.

3. The method of claim 1, wherein the synchronizing comprises:

acquiring electrocardiographic (ECG) formation through an ECG sensor which is connected to the one or more processors;

synchronizing the ECG information, the hemodynamic-related information, the first high-frequency component information and the vibration energy information on the same time axis; and performing heartbeat segmentation on the hemodynamic-related information or the first high-frequency component information into heartbeats based on the ECG information.

4. A cardiac diastolic function assessment method, performed by one or more processors executing one or more computer programs stored in a memory, comprising:

non-invasively and continuously acquiring vibration information on a body surface corresponding to a thoracic cavity of a supine subject using a fiber-optic sensor which is connected to the one or more processors, wherein the fiber-optic sensor is configured to be placed under the subject's body between a left shoulder blade and a right shoulder blade, a sense area of the fiber-optic sensor is at least 20 square centimeters and covers the body surface corresponding to the right shoulder blade of the subject;

preprocessing the vibration information to generate hemodynamic-related information within 9 Hz-45 Hz, comprising filtering, noise removal and signal scaling;

performing second-order differential processing on the hemodynamic-related information to generate second high-frequency component information;

generating vibration energy information by performing energy integration on the hemodynamic-related information, wherein the vibration energy information comprises two energy envelopes in one cardiac cycle, one energy envelope has a higher energy peak and is a systolic energy envelope with a duration as a first-time window, and the other energy envelope is a diastolic energy envelope with a duration as a second-time window, a highest peak of the hemodynamic related information in the same cardiac cycle of the two energy envelopes is located within the first-time window of the systolic energy envelope;

synchronizing the hemodynamic-related information, the second high-frequency component information and the vibration energy information on a same time axis, and performing heartbeat segmentation;

determining, on the second high-frequency component information, in each cardiac cycle, wave clusters within the first-time window as a first wave group, wave clusters within the second time window as a second wave group, and "W"-shaped wave clusters before the first wave group as a third wave group;

determining a first parameter and a second parameter based on the second wave group and the third wave group, the step of determining a first parameter comprising:

on the second wave group of the second high-frequency component information, performing a first "W" waveform search and determining the first parameter as a first amplitude between a second wave trough in the "W" waveform of the second wave group and a first wave peak of the second wave group before or after the second wave trough in the "W" waveform of the second wave group;

on the third wave group of the second high-frequency component information in the same cardiac cycle of the second wave group, performing a second "W" waveform search and determining the second parameter as a second amplitude between a second wave trough in the "W" waveform of the third wave group and a first wave peak of the third wave group before or after the second wave trough in the "W" waveform of the third wave group;

wherein the first parameter comprises a vibration amplitude formed on the body surface of the subject by muscle movement and blood flow movement caused by ventricular filling during early ventricular diastole; and the second parameter comprises the vibration amplitude formed on the body surface of the subject by the muscle movement and the blood flow movement caused by atrial systole during late ventricular diastole; and determining an indicating parameter $I_2$, which is a ratio of the first parameter to the second parameter, and determining the subject to be in an elevated filling pressure if the indicating parameter $I_2$ is greater than a threshold; wherein the threshold depends on a certain population.

5. The method of claim 4, wherein the performing heartbeat segmentation comprises:

performing, on the hemodynamic related information or the second high-frequency component information, a search for the highest peak or a lowest valley with a search interval between 0.6 s and 1 s; and performing heartbeat segmentation based on the searched highest peak or the lowest valley.

6. The method of claim 4, wherein the synchronizing comprises:

acquiring electrocardiographic (ECG) formation through an ECG sensor which is connected to the one or more processors;

synchronizing the ECG information, the hemodynamic-related information, the second high-frequency component information and the vibration energy information on the same time axis; and performing heartbeat segmentation on the hemodynamic-related information or the second high-frequency component information into heartbeats based on the ECG information.

7. A cardiac diastolic function assessment method, performed by one or more processors executing one or more computer programs stored in a memory, comprising:

non-invasively and continuously acquiring vibration information on a body surface corresponding to a thoracic cavity of a supine subject using a fiber-optic sensor which is connected to the one or more processors, wherein the fiber-optic sensor is configured to be placed under the subject's body between a left shoulder blade and a right shoulder blade, a sense area of the fiber-optic sensor is at least 20 square centimeters and covers the body surface corresponding to the right shoulder blade of the subject;

preprocessing the vibration information to generate hemodynamic-related information of 9 Hz-45 Hz, comprising filtering, noise removal and signal scaling;

performing second-order differential processing on the hemodynamic-related information to generate second high-frequency component information;

generating vibration energy information by performing energy integration on the hemodynamic-related information, wherein the vibration energy information comprises two energy envelopes in one cardiac cycle, one energy envelope has a higher energy peak and is a systolic energy envelope with a duration as a first-time window, and the other energy envelope is a diastolic energy envelope with a duration as a second-time window, a highest peak of the hemodynamic related information in the same cardiac cycle of the two energy envelopes is located within the first-time window of the systolic energy envelope;

synchronizing the hemodynamic-related information, the second high-frequency component information and the vibration energy information on a same time axis, and performing heartbeat segmentation;

determining, on the second high-frequency component information, in each cardiac cycle, wave clusters within the first-time window as a first wave group, wave clusters within the second time window as a second wave group, and "W"-shaped wave clusters before the first wave group as a third wave group;

determining a first wave trough of the second wave group after a highest peak of the second wave group of the second high-frequency component information as a first characteristic point, and determining a second wave trough of the third wave group of the second high-frequency component information as a second characteristic point;

determine a first parameter of the second high-frequency component as a first amplitude between the first characteristic point and a first wave peak of the second wave group before or after the first characteristic point on the second high-frequency component information; wherein the first parameter comprises a vibration amplitude formed on the body surface of the subject by muscle movement and blood flow movement caused by ventricular filling during early ventricular diastole;

determining a second parameter of the second high-frequency component as a second amplitude between the second characteristic point and a first wave peak of the third wave group before or after the second characteristic point in the same cardiac cycle on the second high-frequency component information; wherein the second parameter comprises the vibration amplitude formed on the body surface of the subject by the muscle movement and the blood flow movement caused by atrial systole during late ventricular diastole; and determining an indicating parameter $I_2$, which is a ratio of the first parameter to the second parameter, and determining the subject to be in an elevated filling pressure if the indicating parameter $I_2$ is greater than a threshold; wherein the threshold depends on a certain population.

8. The method of claim 7, wherein the performing heartbeat segmentation comprises:

performing, on the hemodynamic related information or the second high-frequency component information, a search for the highest peak or a lowest valley of the hemodynamic related information or the second high-frequency component information with a search interval between 0.6 s and 1 s; and performing heartbeat segmentation based on the searched highest peak or the lowest valley of the hemodynamic related information or the second high-frequency component information.

9. The method of claim 7, wherein the synchronizing comprises:

acquiring electrocardiographic (ECG) information through an ECG sensor which is connected to the one or more processors;

synchronizing the ECG information, the hemodynamic-related information, the second high-frequency component information and the vibration energy information on the same time axis; and performing heartbeat segmentation on the hemodynamic-related information or the second high-frequency component information into heartbeats based on the ECG information.

\* \* \* \* \*